United States Patent
Drevik

(10) Patent No.: US 6,740,069 B2
(45) Date of Patent: May 25, 2004

(54) ABSORBENT ARTICLE SUCH AS A SANITARY NAPKIN, A DIAPER, AN INCONTINENCE GUARD, OR A PANTY-LINER

(75) Inventor: Solgun Drevik, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 231 days.

(21) Appl. No.: 10/015,580

(22) Filed: Dec. 17, 2001

(65) Prior Publication Data

US 2002/0077617 A1 Jun. 20, 2002

Related U.S. Application Data

(60) Provisional application No. 60/255,388, filed on Dec. 15, 2000.

(51) Int. Cl.[7] .................................................. A61F 13/15
(52) U.S. Cl. .................................................. 604/385.01
(58) Field of Search ................... 604/385.01, 385.17, 604/385.22, 385.24, 385.27

(56) References Cited

U.S. PATENT DOCUMENTS

| | | | |
|---|---|---|---|
| 5,688,259 A | * 11/1997 | Osborn et al. | 604/385.01 |
| 5,704,930 A | * 1/1998 | Lavash et al. | 604/685.24 |
| 5,873,869 A | * 2/1999 | Hammons et al. | 604/385.01 |
| D455,829 S | * 4/2002 | Drevik et al. | D24/125 |
| 6,398,770 B1 | * 6/2002 | Drevik | 604/385.01 |
| 6,656,170 B2 | * 12/2003 | Osterdahl et al. | 604/385.17 |
| 6,677,498 B2 | * 1/2004 | Chen et al. | 604/378 |
| 2002/0068915 A1 | * 6/2002 | Drevik et al. | 604/385.01 |
| 2002/0082579 A1 | * 6/2002 | Helmfridsson et al. | 604/385.05 |
| 2002/0087134 A1 | * 7/2002 | Drevik et al. | 604/378 |
| 2002/0156443 A1 | * 10/2002 | Drevik et al. | 604/385.01 |
| 2002/0156450 A1 | * 10/2002 | Drevik et al. | 604/385.101 |
| 2002/0165512 A1 | * 11/2002 | Drevik et al. | 604/380 |
| 2002/0165513 A1 | * 11/2002 | Drevik et al. | 604/385.01 |
| 2003/0125699 A1 | * 7/2003 | Drevik et al. | 604/385.31 |
| 2003/0125700 A1 | * 7/2003 | Drevik | 604/385.31 |
| 2003/0130643 A1 | * 7/2003 | Drevik et al. | 604/385.31 |
| 2003/0139723 A1 | * 7/2003 | Drevik | 604/385.04 |

FOREIGN PATENT DOCUMENTS

| | | |
|---|---|---|
| EP | 0 972 502 | 1/2000 |
| EP | 0 985 396 | 3/2000 |
| WO | WO 99/25282 | 5/1999 |

* cited by examiner

Primary Examiner—Weilun Lo
Assistant Examiner—Michael Bogart
(74) Attorney, Agent, or Firm—Young & Thompson

(57) ABSTRACT

An absorbent article such as a sanitary napkin, an incontinence guard, a diaper, or a panty-liner, has a substantially elongated shape with a longitudinal direction and a transverse direction and exhibits two side edges (9,10), a front edge (11) and a rear edge (12), a front portion (6) and a rear portion (7), and a central portion (8) situated between the front portion (6) and the rear portion (7). The article furthermore includes a liquid-pervious cover layer (2) and a liquid-impervious cover layer (3) and an absorbent body (4), a hump (26) extending in the longitudinal direction and having two longitudinally extending sides, and elastic members (19). The article is characterized in that the hump (26) includes a formation element (27) and the elastic members (19) are arranged along either longitudinally extending side of the hump, wherein the formation element (27) and the elastic members (19) cooperate in shaping the hump (26).

16 Claims, 3 Drawing Sheets

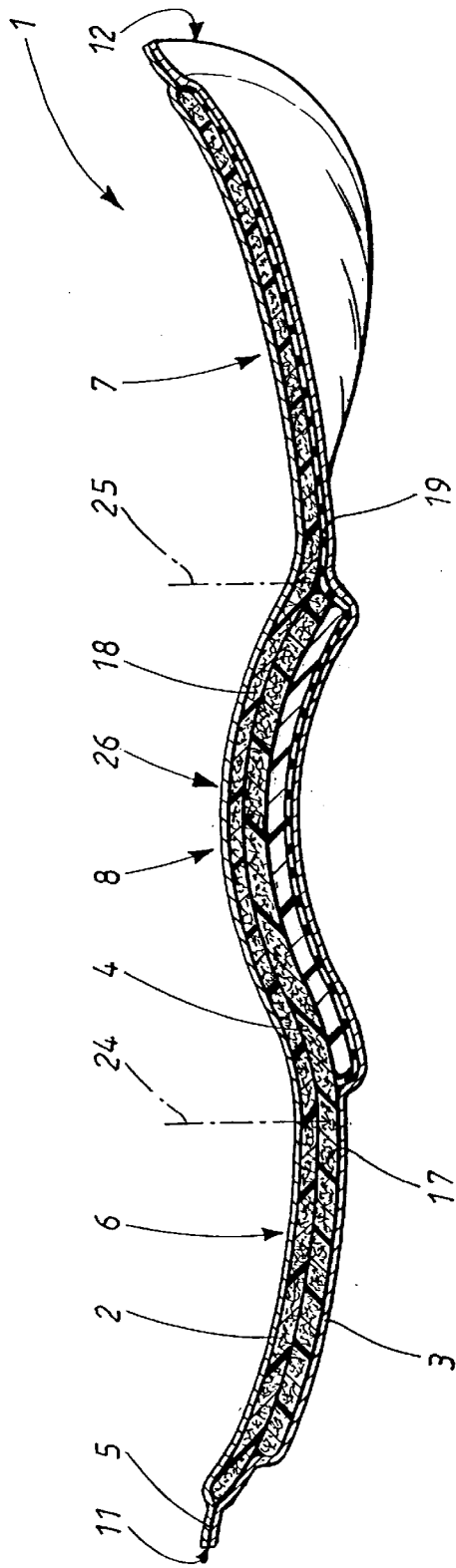
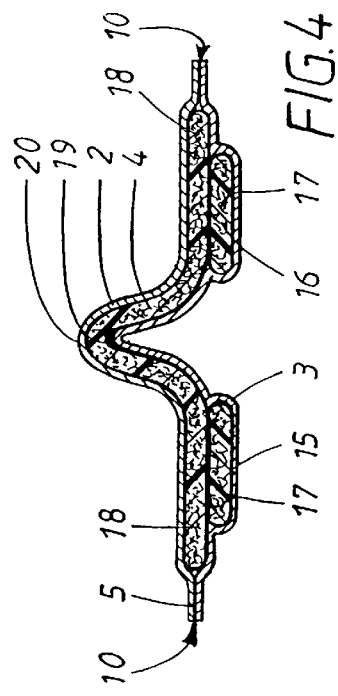
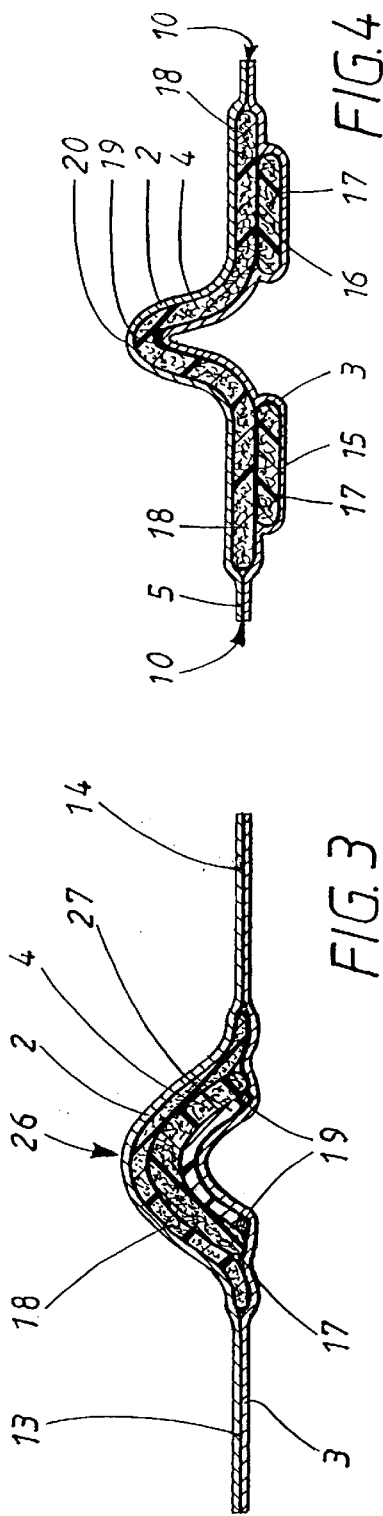

ABSORBENT ARTICLE SUCH AS A SANITARY NAPKIN, A DIAPER, AN INCONTINENCE GUARD, OR A PANTY-LINER

TECHNICAL FIELD

The invention relates to an absorbent article such as a sanitary napkin, an incontinence guard, a diaper, or a panty-liner, which article has a substantially elongated shape with a longitudinal direction and a lateral direction and exhibits two side edges, a front edge and a rear edge, a front portion and a rear portion, and a central portion situated between the front portion and the rear portion, which article further exhibits a liquid-pervious surface layer and a liquid-impervious surface layer and an absorbent body, and a hump extending in the longitudinal direction having two longitudinally extending sides, which article furthermore comprises elastic members.

BACKGROUND ART

Conventional absorbent articles of the type mentioned above usually have a flat shape. Since the female pubic region does not have a corresponding flat appearance, problems can occur when applying and wearing such articles. The contact of the article against the body is not optimum, and when a gap develops there is a great risk of leakage. In order to solve this problem, it has been proposed to make the absorbent articles cup-shaped rather than flat. This shape may provide a better fit to the contours of the body. The cup shape is produced, for example, by arranging an elastic member in the longitudinal edges of the article, or the article is moulded in a cup shape in a more or less stiff material.

A problem with articles of the above-mentioned type is that they do not adapt to the anatomy of the user particularly well, but simply have a general cup-shaped appearance. An article shaped in this way does not provide a good fit against the body. In addition, a gap can easily occur between the user's body and the user's briefs since most women, during menstruation, wear briefs which are of poor quality from the outset or are of poor quality because they are old and worn. Unless either the absorbent article or the briefs are able to maintain a good contact with the user's body, there is a great risk of menstruation fluid leaking past both the absorbent article and the briefs.

EP 985396-A2 discloses an absorbent article having two longitudinally extending elasticated means producing a cup-shaped product, by bending the whole absorbent article. The article further comprising a longitudinal upper absorbent core, placed in the central portion of the article, and a lower absorbent core, which is wider than the upper absorbent core. The two elasticated means runs through the entire article on either side of the upper absorbent core and longitudinally curves the absorbent article convexly downward. The product has a generally curved shape in the longitudinal direction and is stated to provide improved body contact in the central area of the product, thereby reducing the risk of side leakage, as well as a more rapid transport of menstrual fluid from the upper absorbent core to the lower absorbent core.

Even though the longitudinal upper absorbent core provides improved body contact with the body, a problem with a construction of the type mentioned is that the upper absorbent core becomes curved convexly downward in the central portion of the article, which may reduce the body contact in the genital area where the discharge of fluids occur. Another problem is that the upper absorbent core is separated from the lower absorbent core, which may result in that the upper absorbent core and/or the lower absorbent core slide too much in a lateral direction, thereby causing a bad fit and/or inadequate absorbent behaviour.

It is also known absorbent articles comprising a hump being part of the absorbent core as a separate component of the core. The hump may be made from a separate material with special features, placed in or on the absorbent core, or the absorbent core may be manufactured with an additional amount of material, thereby forming the hump as a part of the absorbent core.

A problem with this construction is that the absorbent core is hard to preserve in a desired shape, which means that the hump needs to be manufactured in a special way in order to assume a correct form during use. For instance, if the hump is too soft, it deforms and may flatten out, thereby loosing its intended function, and if the hump is too hard the sanitary napkin may be uncomfortable.

It is also known from WO 99/25282 an absorbent article where an elastic member is arranged in the article and gives the article a cup-shaped part at one end portion and a ridge-like elevation at the other end portion. The elastic member may be arranged in a loop in the front portion, which has a cup-shaped part, and where the elastic member in a loop contributes to giving the front portion its cup shape. The elastic member may also be arranged as a continuous thread or band running through the entire article, and in order to further improve the anatomical fit against the user's body for an article with a ridge-like elevation which extends across both the central portion of the article and across the rear portion thereof, the ridge-like elevation in the end portion has a steeper inclination towards the centre line of the article than does the ridge-like elevation in the central portion, as seen from a long side of the article. The cup shape of the front portion will surround the mons pubis during use, and the ridge-like elevation of the rear portion will fit in the cleft between the user's buttocks.

Even though the ridge-like elevation which extends across both the central portion of the article and across the rear portion thereof provides improved body contact in the central portion and the rear portion of the article, a problem with a construction of the type mentioned is that the elastic member bends the entire absorbent body. If the absorbent body is too soft, the elastic member bends the article too much, which may result in a bad fit, and if the absorbent body is too stiff the central portion may become bulky and uncomfortable for the user. A bulky or wrinkled ridge-like elevation may not be high enough and/or thin enough to provide sufficient protection for leakage of body fluids between the buttocks of the user when the user is lying down on his back. Another problem is that the ridge-like elevation consists of the thick and relatively stiff absorbent body, which give the ridge-like elevation a triangular shape, which makes the ridge-like elevation relatively wide and thereby hard to fit between the buttocks of a user.

Whilst previously known absorbent articles provide relatively good leakage protection and relatively good fit, a need still exists for an absorbent article which further increases the comfort by being small and flexible, and also further reduces the risk of leakage of body fluids by improved contact between the article and the body of the user, especially in the genital area, i.e. an article that has an anatomically correct shape in the wetting area, and that the article still is easy and cheap to manufacture. It is therefore an object of the present invention to provide an absorbent article that meets these requirements.

DISCLOSURE OF INVENTION

The object of the invention is to remedy the above mentioned problems and to make available an absorbent article which provides a good fit against the user's body and has an anatomically correct shape in the wetting area, and which article is comfortable to use and that reduces the leakage of body fluids.

The absorbent article may be a sanitary napkin, an incontinence guard, a diaper, or a panty-liner, which article has a substantially elongated shape with a longitudinal direction and a transverse direction and exhibits two side edges, a front edge and a rear edge. The absorbent article also has a front portion and a rear portion, and a central portion situated between the front portion and the rear portion. The article furthermore exhibits a liquid-pervious cover layer and a liquid-impervious cover layer and an absorbent body, and a hump extending in the longitudinal direction having two longitudinally extending sides. The absorbent article also comprises elastic members.

The invention is characterized in that the hump comprises a formation element extending in the longitudinal direction and having two longitudinally extending sides, and that the elastic members are arranged along either longitudinally extending side of the formation element, wherein the formation element and the elastic members cooperate in shaping the hump. The formation element is advantageously placed between the liquid-impervious cover layer and the absorbent body and the elastic members that run on either side of the formation element, exert a lateral force on the formation element, thereby curving the formation element convexly upward, which elevates the above lying layers into the shape of the longitudinal hump in the central portion of the article.

In one embodiment of the invention the rear portion of the absorbent body comprises a layer that is split in a first leg and a second leg with a gap between the legs where an angle α is defined between the first leg and the second leg, and that the elastic member also is placed between the first leg and the second leg extending essentially in the longitudinal direction. The elastic members that run in the rear portion bend the rear portion in a somewhat parabolic shape, deforming parts of the absorbent article that lies between the first leg and, thereby forming a ridge-like elevation between the first leg and the second leg.

Further descriptions of the invention will be presented in the subsequent text.

BRIEF DESCRIPTION OF DRAWINGS

FIG. 2 shows a cross sectional side view of the absorbent article in FIG. 1 taken along a line II—II in FIG. 1.

FIG. 3 shows a cross sectional backside view of the absorbent article in FIGS. 1 and 2 taken along a line III—III in FIG. 1.

FIG. 4 shows a cross sectional backside view of the absorbent article in FIGS. 1–3 taken along a line IV—IV in FIG. 1.

MODES FOR CARRYING OUT THE INVENTION

Figure 1:
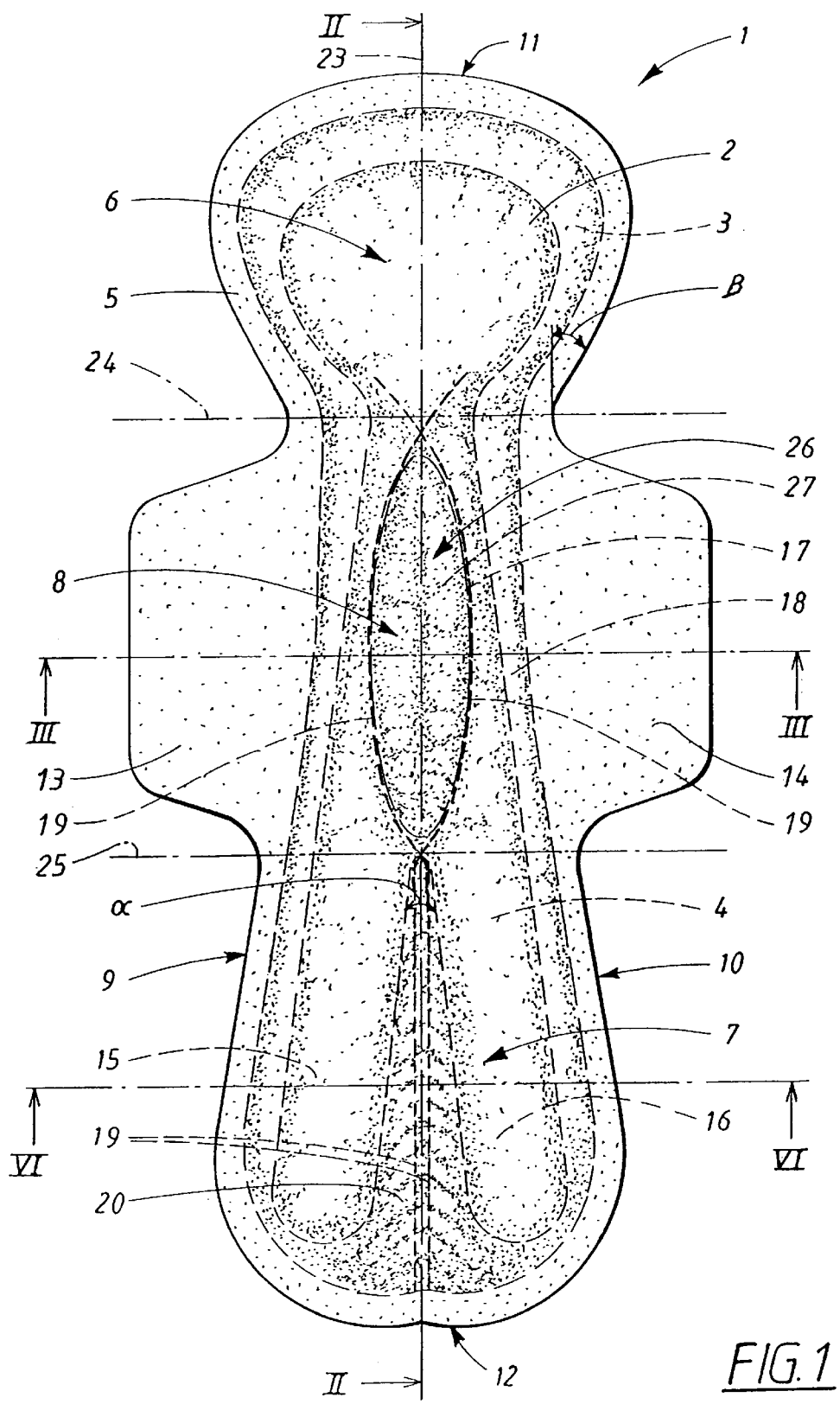
FIG. 1 shows a top view of an absorbent article according to one embodiment of the invention.

The absorbent article according to a first embodiment of the invention is shown in FIGS. 1, 2, 3 and 4, and will be described hereupon. The embodiments presented shall not be seen as limiting for the invention, but merely as descriptions for facilitating the understanding of the invention.

The absorbent article 1 comprises a liquid-pervious cover layer 2 arranged on the side of the absorbent article 1 which, during use, is intended to face the user, a liquid-impervious cover layer 3 arranged on the side of the absorbent article 1 which, during use, is intended to be facing away from the user, and an absorbent body 4 enclosed between the two cover layers 2, 3.

The absorbent article 1 is substantially hourglass-shaped and thereby exhibits a front portion 6, intended to be directed forward on the user during use, a rear portion 7, intended to be directed backwards on the user during use, and an intermediate, narrower central portion 8 intended to be applied in the groin area of the user. Furthermore, the absorbent article 1 has two concavely-curved side edges 9, 10, a convexly-curved front edge 11, and a similarly convexly-curved rear edge 12.

The segmentation of the absorbent article into a front portion 6, a rear portion 7, and a central portion 8, should not be understood as implying that there are sharp limits between the different portions 6–8, but is primarily intended to facilitate the description of the absorbent article with reference to the differences which are present between the different portions 6–8 depending on how they are intended to be placed in relation to the body of a user. Thus, the transition between the different portions 6–8 does not take place at fixed transverse lines, but rather within transitional areas situated at a distance of approximately one third of the length of the absorbent article from the front edge 11 and the rear edge 12 of the absorbent article, respectively. But, when using longer products the ratio between the central portion and the front portion may be two to five, which may be true also for the ratio between the central portion and the rear portion. In this manner, the central portion 8 constitutes the part of the absorbent article which, in use, is intended to receive and absorb the major part of the liquid which during use is emitted to the absorbent article.

The two cover layers 2, 3 are mutually connected outside the absorbent body 4 and form a protruding edge 5 around the entire periphery of the absorbent article. The joining of the cover layers may take place in any suitable way, such as by means of gluing, sewing, or welding either with heat or ultrasonically.

The absorbent article 1 according to the invention is designed with a front portion 6 which is wider than the central portion 8, and with a central portion 8 which is narrower than both the front portion and the rear portion. In order to obtain an absorbent article that has a good fit and that feels comfortable for the user, it is essential that the napkin has a shape which to a very high degree is adapted to the anatomy of the user. Thus, it is of particularly great importance that the width of the first absorbent layer 17, at least in the front part of the central portion 8, does not exceed approx. 40 mm. One reason why the front portion 6 is wider than the central portion 8 is that the wider front portion 6 together with the narrower central portion 8 forms around the body of the user, and somewhat "hooks" the absorbent article against the legs of the user, thus makes the absorbent article able to stay in place against the body of the user. The wider front portion 6 is preferably in a somewhat oval shape. One reason for this is that the oval shaped front portion 6, when in use, is bent inwardly forming a cup-shaped bowl, i.e. the upwards bending of the front portion 6, in relation to the central portion 8, does not occur along a sharp folding line, but instead the curvature is continuous in the longitudinal direction of the absorbent article. In this manner, the front portion 6 forms a softly rounded bowl, which conforms very well to the anatomy of the user. Furthermore, the oval shape of the front portion 6 also gives a large absorption area/volume for the absorption body 4.

Furthermore, the absorbent article 1 exhibits two longitudinal side edges 9, 10, a transverse concavely-curved front edge 11 and a transverse convexly-curved rear edge 12. The absorbent article is designed in such a way that, in the front portion of the central portion 8, there is a first cross-sectional line 24, extending in the transversal direction of the absorbent article, which intersects the side edges 9, 10 of the absorbent article. At the first cross-sectional line 24, the side edges 9, 10 change inclination in relation to the longitudinal centre line 23, whereby the width of the absorbent article increases in a direction towards the front edge 11, whereby the front portion 6 exhibits a maximum width, which exceeds the width of the central portion 8 at the first cross-sectional line 24. The maximum width of the front portion 6 is suitably at least twice the width of the central portion 8 at the first cross-sectional line 24. The inclination of the side edges 9, 10 at the front portion 6 is defined by an angle β between each respective side edge 9, 10 and a longitudinal line parallel to the centre line 23, whereby β is between 30° and 90° and whereby the width of the central portion 8 of the first absorbent layer 17 at the first cross-sectional line 24, is between 15 and 45 mm and preferably between 20 and 40 mm. All data mentioned above is mentioned as being valid for the whole absorbent article, but that is only true if the contour of the absorbent article closely follows the contour of the first absorbent layer 17.

The absorbent article according to the invention has a longitudinal hump 26, with two longitudinal extending sides, which is created in the central portion 8 of the article, by using a formation element 27, with two longitudinally extending sides, placed under the absorbent body 4, together with two elastic members 19. The two elastic members 19 run jointly through the rear portion 7, and are split into two separate elastic members 19 before the formation element 27 and placed on either side of the formation element 27, after which formation element 27 the two elastic members 19 are joint together in at least one point. Advantageously the elastic members 19 may be crossed both before and after the formation element 27. The formation element 27 is formed in such way that the two elastic members 19 stress the formation element 27 with lateral forces, thereby curving the formation element 27 convexly upward, which elevates the above lying layers, i.e. the absorbent body 4 and the liquid-pervious cover layer 2 into the shape of the longitudinal hump 26 in the central portion 8 of the article. Thus, the two elastic members 19 complement the pre-formed formation element 27 in shaping the longitudinal hump 26. The two elastic members 19 are preferably pre-stressed before attached to the absorbent article, preferably fastened to the liquid-impervious cover layer 3 in close contact with either side of the formation element 27. The elastic members may be placed in, or between, or/and against any one of the layers that builds the absorbent article, dependent on desired features of the absorbent article, but from a fastening and manufacturing point of view, they are advantageously fastened on the liquid-impervious layer. Advantageously, the longitudinal hump 26 has an oval shape in a direction from the front portion 6 to the rear portion 7, as seen from the above (FIG. 1), and a form that may be described as a soft cornered parallelepiped, as seen from the side (FIG. 2), and a soft cornered triangle, as seen from the rear (FIG. 3). Thus, the longitudinal hump 26 narrows towards the rear portion 7 of the absorbent article.

The formation of the longitudinal hump in the central portion enhances the contact between the genital are of the user and the absorbent article, thereby reducing the risk of leakage outside the napkin. The elastic members support the formation of the longitudinal hump also during use, thereby reducing the risk of a wrongly deformed sanitary napkin in the central portion, thereby forming an absorbent article that has the right form in the wetting area.

Dependent on desired features of the hump, the shape of the formation element may be in another shape as the one described above, for instance oval or rectangular as seen from either the rear or from the side.

Wadding, foam, cross-linked cellulose fibres, or a mixture of the mentioned fibres may advantageously primarily constitute the formation element 27, which preferably have the abilty of springing back in both dry and wet conditions. Examples of other useful materials are fluff pulp, unbound fibre, or formed materials in layers that are rolled so as to form the forming element 27.

Further characteristics of the formation element 27 are that it may be of a resilient material, an absorbent material or a non-absorbent material. The formation element may also have a longitudinally bending indication line along the centre line, in order to more easily get the desired shape of a soft cornered triangle, as seen from the rear (FIG. 3).

The width of the hump is less than the width of the absorbent body (4), and the length of the hump is 20–120 mm, and the height of the hump is maximum 50 mm, preferably 5–20 mm.

The absorbent body 4 may advantageously comprise different layers of different types of absorbent material. FIG. 1 shows an absorbent body 4 comprising two different layers of absorbent material, a first absorbent layer 17 and a second absorbent layer 18. The first absorbent layer 17 is arranged between the liquid-impervious cover layer 3 and the second absorbent layer 18, and the second absorbent layer 18 is arranged between the first absorbent layer 17 and the liquid-pervious cover layer 2. Advantageously, the second absorbent layer 18 is a fast material that transports fluids well, and the first absorbent layer 17 has a good capacity for storing fluids.

According to the described embodiment of the invention the first absorbent layer 17 is more rigid than the second absorbent layer 18. But, the material of the first absorbent layer 17 need not be more rigid than the second absorbent layer 18 per se, i.e. the first absorbent layer 17 may be manufactured in such way that it becomes more rigid than the second absorbent layer 18, for instance by glue lamination of several layers of the same or different material or another suitable choice of manufacturing. The first absorbent layer 17 serves as a formation portion, whereby the area of the first absorbent layer 17 that lies substantially within the area of the rear portion 7 is split into a first leg 15 and a second leg 16 from a point in the vicinity of a second cross-sectional line 25. Said second cross-sectional line 25 extends in the transversal direction of the absorbent article, intersecting the side edges 9,10 of the absorbent article. The legs 15, 16 form an angle α in the point where the legs are split. The angle α between the legs 15,16 is between 10°–120° preferably 15°–40°, and the length of the legs are between 20–350 mm, preferably 50–150 mm. The second cross-sectional line 25 is placed in the imaginary area where the rear portion 7 meets the central portion 8.

The elastic members 19 are placed between the first leg 15 and the second leg 16, as continuous threads or a band running mainly along the centre line 23, from a point in the vicinity of where the centre line 23 meets the protruding edge 5 on the rear edge 12 to a point beyond the point where the absorbent body (4) is split into the two legs 15, 16, and before the point where the longitudinal hump starts. The elastic members 19 are advantageously fastened to the liquid-impervious cover layer 3, either entirely or partially. The two legs 15, 16 consist of the more rigid first absorbent layer 17 and is covered with the second absorbent layer 18. The part where the elastic members 19 run in the rear portion 7 consists of the less rigid second absorbent layer 18. Both the absorbent layers 17, 18 are enclosed by the liquid-pervious cover layer 2 and the liquid-impervious cover layer 3.

If the article lacks a protruding edge 5, the elastic members 19 are placed between the first leg 15 and the second leg 16, as continuous threads or a band that runs mainly along the centre line 23, from a point in the vicinity of where the centre line 23 meets the rear edge 12, to a point beyond the point where the absorbent body (4) is split into the two legs 15, 16.

The elastic members 19 bend the rear portion 7 in a somewhat parabolic shape, which further improves the anatomical fit against the user's body. When the elastic members 19 bend the rear portion 7, the second absorbent layer 18 and the liquid-pervious cover layer 2 will be somewhat deformed in such way so as to give rise to the forming of a ridge-like elevation 20 between the first leg 15 and the second leg 16. Since the second absorbent layer 18 is less rigid than the first absorbent layer 17, the rigid legs 15, 16 will be drawn together and will not deform significantly in the lateral direction, which enhances the deformation of the less rigid second absorbent layer 18 and the liquid-pervious cover layer 2, thereby giving rise to a well-defined high and relatively narrow ridge-like elevation 20 in the rear portion 7 of the absorbent article 1. The lack of lateral deformation of the legs 15, 16 also gives rise to a unique shape of the ridge-like elevation 20, where the ridge-like elevation 20 starts from the inside edges of the relatively flat legs 15, 16, seen from the cross sectional backside view in FIG. 4. The ridge-like elevation 20 rises from the inside edges of the legs 15, 16 in a steep upward inclination towards the centre line 23. The ridge-like elevation together with the relatively flat legs 15, 16 may be described as being somewhat in the shape of a cross section of a "Wizard's hat" with a cone shaped top standing on a flat brim, which clearly can be seen in FIG. 4. Since the legs 15, 16 are relatively flat in the lateral direction, the ridge-like elevation 20 becomes narrow and high. The ridge-like elevation 20 will therefore fit snugly in the cleft between the buttocks of the user and will effectively stop and absorb any body fluids that flows between the buttocks, especially advantageous for a user lying down on her back. The relatively flat legs 15, 16 of the absorbent article 20 will serve as a stop against the buttocks of the user, thereby preventing that more of the absorbent article 1 deforms and slides in between the buttocks of the user. The shape of the ridge-like elevation 20 in the rear portion 7 has a steep inclination towards the centre line 23 of the article 1, as seen from a long side of the article. The inclination towards the centre line 23 improves the anatomical fit against the user's body for an article with a ridge-like elevation, which extends across the rear portion thereof.

As is clear from the description above and FIGS. 1–4, the ridge-like elevation 20 transitions into the narrow part of the longitudinal hump 26, thereby combining all the advantages with the longitudinal hump 26 and the ridge-like elevation 20 respectively mentioned above.

One important feature of the described embodiment of the invention is that the area between the legs 15, 16 of the absorbent article 1 is less rigid than the areas surrounding that area, i.e. the legs 15, 16. The absorbent article 1 may be manufactured in a number of different ways dependent on the use and/or user demands. To change the features of the sanitary napkin it is possible to work with a number of parameters, for instance the tension of the elastic members 19, where and how the elastic members 19 are fastened, the angle $\alpha$ between the legs 15, 16 and the relative difference in stiffness between the area situated between the legs and the area surrounding that area. All the mentioned parameters give rise to a number of ridge-like elevations according to the present invention, but in different heights, lengths, widths, inclinations and angles, all dependent on the wanted feature. However, independent of how the parameters are changed, the shape of the absorbent core together with the elastic members 19 and the relative difference in stiffness between the area between the legs 15, 16 and the areas surrounding that area, give rise to the narrow ridge-like elevation 20 in the unique shape of a "Wizard's hat" according to the embodiment, as shown in FIG. 4. It is more important that the ridge-like elevation is narrow than that it is high, due to the fact that the most important area to fit the ridge-like elevation into, is the area between the buttocks of a user, in close vicinity to the vaginal area of the user.

The ridge like elevation may be described as having a top portion constituting an upper part of the ridge like elevation and that the width of the ridge-like elevation 20 is 0.1–20 mm, preferably 1–8 mm, at the top portion of the ridge-like elevation (20), and that the length of the ridge-like elevation is at least 10 mm. The width of the ridge-like elevation 20 at the top portion corresponds to the dimension of the elastic members and the dimension of the absorbent layer that covers the elastic member, i.e. the second absorbent layer in the described embodiment.

The material of the liquid-pervious cover layer 2 may, for instance, be a perforated plastic film, a plastic scrim or a textile material, a fibrous wadding, a nonwoven material or a laminate of, for instance, a perforated plastic film and a nonwoven sheet. The laminate may be made of any materials suitable for the chosen purpose. The plastic material is typically thermoplastic, such as polyethylene or polypropylene. The expression "nonwoven material" refers to a nonwoven fibrous web. Suitable nonwoven materials may consist of natural fibres, such as cellulose or cotton, or synthetic fibres such as polyethylene, polypropylene, polyester, polyurethane, nylon or regenerated cellulose. Naturally, it is also possible to use nonwoven materials made from fibre blends.

The liquid-pervious cover layer 2 is intended to receive and conduct the liquid into the absorbent body 4. Furthermore, the cover layer 2 should be soft and pleasant against the body of the user, as well as being able to prevent so-called rewetting, i.e. that absorbed body exudate forces its way back towards the skin of the user. For reasons of comfort, and in order to avoid skin irritation, it is important that the surface on the portion of the absorbent article which contacts the skin of the user be maintained as dry as possible during use. Furthermore, a dry surface on the absorbent article is perceived by the user as being cooler and more pleasant during use, and is both from a purely visual aspect, and when handling the absorbent article when this is to be changed, more attractive than a soiled, wet surface. But, in order to avoid irritation of the mucous membranes in the genital parts, the parts of the absorbent article that are in contact with the mucous membranes preferably may be somewhat moist, for instance parts of the ridge-like elevation 20. The parts of the absorbent article that are in contact with the mucous membranes may be constituted of a hydrophilic material, either partly or entirely.

It is not necessary for all embodiments of the invention that the liquid-pervious cover layer 2 does in fact constitute a separate material layer. The liquid-pervious cover layer may, for instance, constitute an integral part of an absorbent body. Thus, it is conceivable that the liquid-pervious cover layer be omitted should the absorbent body comprise an absorbent foam layer or another absorbent material being sufficiently coherent not to disintegrate during use. Furthermore, an absorbent nonwoven material may be utilized, which may be a component of an absorbent body and at the same time constitute a liquid-pervious cover layer.

The liquid-impervious cover layer 3 consists of a liquid-impermeable material. Thin, liquid-impervious plastic films are suitable for the purpose. It is, however, also possible to use materials which are originally liquid-pervious but which have been provided with a coating of plastic, resin, or other liquid-impervious material. In this manner, leakage of liquid from the bottom side of the absorbent article is prevented. The liquid-impervious cover layer 3 may accordingly consist of any material which is skin-friendly and which fulfils the criteria of liquid-impermeability. Examples of materials, which are suitable as barrier layers, are plastic films, non-woven materials and different types of laminates. Useful plastic films are, for instance, those that consist of polyethylene, polypropylene, or polyester. Alternatively, the liquid-impervious cover layer 3 may consist of a laminate of a liquid-impermeable plastic layer facing the absorbent body and a nonwoven sheet facing the underclothing of the user. Such a construction provides a leakage-proof barrier layer with a textile feel.

As with the liquid-pervious cover layer 2, it is not necessary that the liquid-impervious cover layer 3 is constituted by a separate layer. Accordingly, it is conceivable that the liquid-impervious cover layer 3 constitutes an integral part of an absorbent material, for instance an absorbent foam layer with a liquid-impervious surface.

The absorbent body 4 may advantageously be primarily constituted by cellulose fluff pulp. The fluff may be present in the form of reels, bales or sheets which are dry shredded or wet formed and transformed in a fluffed state into a pulp mat, with or without the admixture of so-called super-absorbents, which are polymers with an ability to absorb several times their own weight of water or body exudate. Examples of other useful materials are different types of natural fibres such as cotton fibres, peat, or the like. It is, of course, also possible to utilize absorbent synthetic fibres, or blends of natural fibres and synthetic fibres. The absorption material may furthermore include further components, such as liquid-distributing members or binders such as e.g. thermoplastic fibres which have been heat-treated in order to bind short fibres and particles into a coherent unit. It is also possible to utilize different types of absorbent foam materials in the absorbent body 4.

FIG. 4 shows the legs 15, 16, consisting of the first absorbent layer 17, as lying under the second absorbent layer 18, each leg forming a protruding part towards the liquid-impervious cover layer 3, with a relatively flat lateral liquid-pervious cover layer 2 surface in the area. This is due to the manufacturing process, which was used to produce the article. Another choice of manufacturing process could give rise to protruding parts, formed by the legs 15, 16, and the second absorbent layer 18, towards the liquid-pervious cover layer 2, with a relatively flat lateral liquid-impervious cover layer 3 surface in the area, i.e. the opposite of what is shown in FIG. 4. regarding the areas that include the legs.

Regarding the materials in the absorbent article, an example is drawn from the testing of the present invention and will be presented in the following text. The material in the first absorbent layer 17 expediently consists of a single layer of High Density Air Laid (HDA) from domestic manufacturing with a stiffness of approx. 5.4 Newton. The second absorbent layer 18 expediently consists of a single layer of 100 g Low Density Air Laid (LDA) with a stiffness of approx. 1.15 Newton. The stiffness is measured according to the CIRCULAR BEND PROCEDURE which is described in EP-A-0 336 578, which publication is hereby included as a reference. This described method is a modification of ASTM D 4032-82 and involves simultaneous deformation of a material in several directions, one of the surfaces of the specimen becoming concave and the opposite surface becoming convex, The method thus gives a force value which is a measure of the flexural resistance, or the average stiffness in all directions. In this exemplified embodiment, the relative difference in stiffness between the second absorbent layer 18 and the first absorbent layer 17 gives a ratio of 1.15/5.4, which is the same as approx. 21%. This shall only be seen as an illustration, and shall not be seen as limiting for the invention. A change in the materials will of course give other results, which may advantageously be used in some cases, for instance the fact that the second absorbent layer 18 covers the first absorbent layer 17 also in the rear portion, enhances the difference in relative stiffness between the area between the legs 15, 16 and the area that constitute the legs 15, 16.

The elastic members 19 is pre-stressed before it is attached to the absorbent article 1, with a force between 0.05–0.4 Newton, preferably between 0.1–0.3 Newton.

Figure 5:
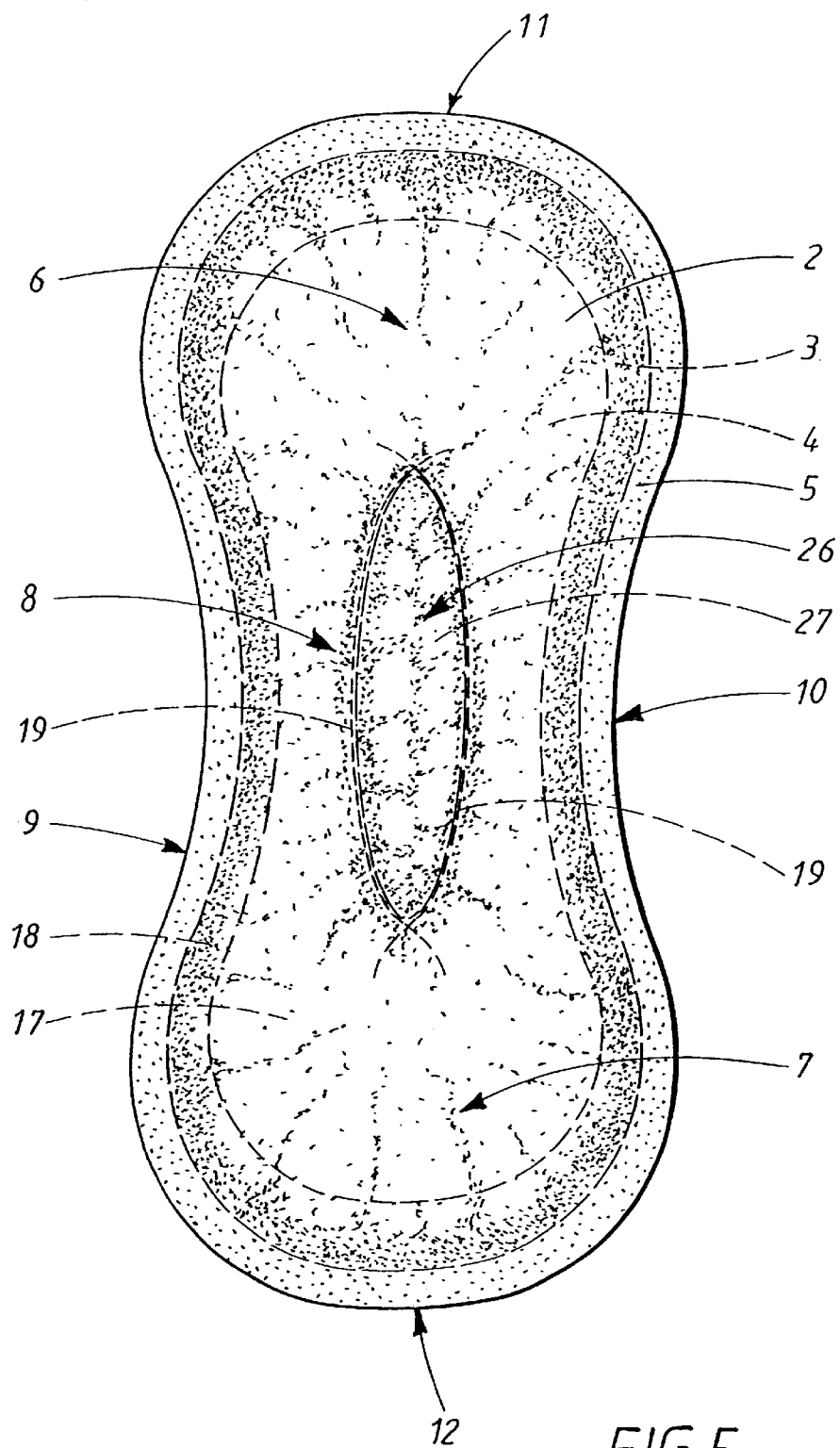
FIG. 5 shows a top view of an absorbent article according to a second embodiment of the invention.

A second embodiment of the invention is shown in FIG. 5, where the elastic members 19 are placed only in the central portion 8 on either side of the formation element 27 in order to achieve the same function as described above regarding the forming of the hump 26. The elastic members 19 may, both in front of and behind the formation element 27, run jointly a small distance in the longitudinal direction, and may advantageously be crossed both in front of and behind the formation element 27. In the second embodiment the sanitary napkin has an oval shape and lacks the above-described legs 15, 16. FIGS. 2 and 3 are still valid for exemplifying the central portion in the second embodiment. In this embodiment as well as for absorbent articles of different shapes than the first described embodiment, the width of the first absorbent layer 17 in the front part of the central portion 8 may exceed approx. 40 mm.

In yet a further embodiment of the invention (not shown) the elastic members 19 may be substituted by a continuous elastic thread or band running through the entire absorbent article 1 in order to bend also the front portion and the central portion in a parabolic shape, which enhances the fit against the body of the user as well as enhancing the "hooking" of the front portion 6 against the legs of the user, which enhances the ability of the absorbent article to stay in place during use. The elastic thread or band is split in the same way as the elastic members 19, in order to achieve the same function as described above regarding the forming of the hump.

Depending on how the elastic members 19, or its substitute, are fastened in the absorbent article 1 and stretched in different parts of the absorbent article 1, the elastic members 19 may deform different parts of the central portion and thereby, for instance, create an extension of the ridge-like elevation 20 in the rear portion 7, into the central portion. This is in order to further improve the anatomical fit against the user's body for an article with a ridge-like elevation, which extends across both part of the central portion of the article and across the rear portion thereof. The ridge-like elevation in the end portion preferably has a steeper inclination towards the centre line of the article than does the ridge-like elevation in the central portion, when seen from a long side of the article. To enhance the ridge-like elevation in the central portion, the absorbent core 4 may be slit either entirely or partially.

The invention should not be regarded as being limited to the herein-described embodiments, instead a number of further variants and modifications are conceivable within the scope of the claims. For instance, the invention comprises all types of absorbent articles, which are sized to be substantially accommodated in the groin area of a user. Furthermore, all conceivable combinations of the described embodiments are intended to be embraced by the invention.

The elastic members may comprise more than one elastic element, which together fulfil the same purpose as the two single elastic members described in the embodiments above.

The absorbent article may also include an elastic member that runs in the longitudinal direction through the entire article and that is split in at least two half circle shaped parts in the front portion, which split half circle shaped elastic parts give the article a cup-shaped part at the front portion of the absorbent article, a longitudinal hump in the central portion and a ridge-like elevation in at least the rear portion.

The elastic member may also be arranged in a loop in the front portion, which may or may not be pre-cup-shaped, and the arrangement of the elastic member in a loop contributes to give the front portion its cup shape.

The absorbent article may also include side elastics that run in the longitudinal direction, either partially or through the entire article.

Furthermore, all conceivable types of blends and combinations of material layers may be used.

The absorbent may be equipped with fastening means on both the liquid-impervious layer and the wings.

The absorbent article need not have a protruding edge nor does it need to have wings. The invention may thus be used on a number of different forms, for instance an oval shape or rectangular shape.

What is claimed is:

1. Absorbent article which has a substantially elongated shape with a longitudinal direction and a transverse direction and exhibits two side edges (9, 10), a front edge (11) and a rear edge (12), a front portion (6) and a rear portion (7), and a central portion (8) situated between the front portion (6) and the rear portion (7), which article furthermore comprises a liquid-pervious cover layer (2) and a liquid-impervious cover layer (3) and an absorbent body (4), and a hump (26) extending in the longitudinal direction and having two longitudinally extending sides, which article furthermore comprises elastic members (19), characterized in that the hump (26) comprises a formation element (27) extending in the longitudinal direction and having two longitudinally extending sides, and that the elastic members (19) are arranged along either longitudinally extending side of the formation element (27) wherein the formation element (27) and the elastic members (19) cooperate in shaping the hump (26).

2. Absorbent article according to claim 1, characterized in that the formation element (27) is placed between the liquid-impervious cover layer (3) and the absorbent body (4).

3. Absorbent article according to claim 2, characterized in that the elastic members (19) that run on either side of the formation element (27), exert a lateral force on the formation element (27), thereby curving the formation element (27) convexly upward, which elevates the above lying layers (2, 4) into the shape of the longitudinal hump (26) in the central portion (8) of the article.

4. Absorbent article according to claim 1, characterized in that the rear portion (7) of the absorbent body (4) comprises a layer (17) that is split in a first leg (15) and a second leg (16) with a gap between the legs (15, 16) where an angle α is defined between the first leg (15) and the second leg (16), and that the elastic member (19) also is placed between the first leg (15) and the second leg (16), which elastic member (19) essentially extends in the longitudinal direction.

5. Absorbent article according to claim 4, characterized in that the elastic members (19) that run also in the rear portion (7) bend the rear portion (7) in a parabolic shape, deforming parts of the absorbent article that lie between the first leg (15) and (16), thereby forming a ridge (20) between the first leg (15) and the second leg (16).

6. Absorbent article according to claim 5, characterized in that the elastic members (19) run jointly along a centre line (23) of the absorbent article, from a point in the vicinity of where the centre line (23) meets the rear edge (12), to a point in the vicinity of the formation element (27).

7. Absorbent article according to claim 5, characterized in that the elastic members (19) run along the centre line (23), through the entire absorbent article, except for the part where the elastic members (19) are split and are arranged along either longitudinally extending side of the formation element (27).

8. Absorbent article according to claim 7, characterized in that the elastic members (19) are split into at least two elastic parts in the front portion (6).

9. Absorbent article according to claim 4, characterized in that the elastic members (19) are placed in or between any of the layers that build the absorbent article 1.

10. Absorbent article according to claim 4, characterized in that the angle α is between 10°–120°.

11. Absorbent article according to claim 4, characterized in that the length of the legs (15, 16) is 20–350 mm.

12. Absorbent article according to claim 4, characterized in that the length of the ridge is at least 10 mm.

13. Absorbent article according to claim 4, characterized in that the ridge has a top portion constituting an upper part of the ridge that the width of the ridge (20) is 0.1–20 mm at the top portion of the ridge (20).

14. Absorbent article according to claim 1, characterized in that the width of the hump is less than the width of the absorbent body (4).

15. Absorbent article according to claim 1, characterized in that that the length of the hump is 20–120 mm.

16. Absorbent article according to claim 1, characterized in that that the height of the hump is at most 50 mm.

* * * * *